US009549952B2

(12) United States Patent
Jung et al.

(10) Patent No.: US 9,549,952 B2
(45) Date of Patent: Jan. 24, 2017

(54) LIGNIN MICROCAPSULE AND METHOD OF PRODUCING THE SAME

(71) Applicant: Korea Institute of Science and Technology, Seoul (KR)

(72) Inventors: Yong Chae Jung, Wanju-gun (KR); Eun Sil Lee, Wanju-gun (KR); Hye Jin Yoo, Wanju-gun (KR); Sang Hyun Lee, Wanju-gun (KR); Junyeon Hwang, Wanju-gun (KR); Cheol-Min Yang, Wanju-gun (KR); Min Park, Wanju-gun (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 14/887,000

(22) Filed: Oct. 19, 2015

(65) Prior Publication Data

US 2016/0120816 A1    May 5, 2016

(30) Foreign Application Priority Data

Oct. 31, 2014    (KR) .................. 10-2014-0149941

(51) Int. Cl.
*A61K 9/16*    (2006.01)
*A61K 33/44*    (2006.01)
*H01L 51/00*    (2006.01)
*A61K 9/50*    (2006.01)

(52) U.S. Cl.
CPC ............. *A61K 33/44* (2013.01); *A61K 9/1652* (2013.01); *A61K 9/5031* (2013.01); *H01L 51/0048* (2013.01)

(58) Field of Classification Search
CPC .................................................. A61K 9/1652
See application file for complete search history.

(56) References Cited

U.S. PATENT DOCUMENTS

| 8,816,007 B2 | 8/2014 | Zhang et al. |
| 2010/0008961 A1 | 1/2010 | Takeko |
| 2013/0137626 A1 | 5/2013 | Last et al. |

FOREIGN PATENT DOCUMENTS

| JP | 2008-119684 A | 5/2008 |
| KR | 10-2009-0043726 A | 5/2009 |
| KR | 10-2013-0069568 A | 6/2013 |
| KR | 10-1449248 B1 | 10/2014 |

OTHER PUBLICATIONS

White, Scott R., et al. "Autonomic healing of polymer composites." Nature 409.6822 (2001): 794-797.
Rochez, Olivier, et al. "Dispersion of multiwalled carbon nanotubes in water by lignin." Journal of Materials Science 48.14 (2013): 4962-4964.
Tortora, Mariarosaria, et al. "Ultrasound driven assembly of lignin into microcapsules for storage and delivery of hydrophobic molecules." Biomacromolecules 15.5 (2014): 1634-1643.

*Primary Examiner* — Carlos Azpuru

(57) ABSTRACT

Disclosed are lignin microcapsules including lignin as a shell material and at least one of oil and a carbonaceous material as a core material. The lignin microcapsules may be formed by carried out polymerization in an oil-in-water emulsion including lignin, oil and water and further including a carbonaceous material. Since lignin has a phenol structure, the microcapsules including lignin may be formed to have antibacterial property. Thus, the lignin microcapsules may be used widely in various fields, such as additives for composite materials.

11 Claims, 19 Drawing Sheets

(a)          (b)

(c)

LIGNIN MICROCAPSULE AND METHOD OF PRODUCING THE SAME

DESCRIPTION ABOUT NATIONAL SUPPORT RESEARCH AND DEVELOPMENT

This study was supported by Ministry of Science, ICT and Future Planning, Republic of Korea (Convergence commercialization research project, Project No. applied commercialization-13-21-KAERI and KIST Jeonbuk branch research project, Project No. 2Z04270) under the superintendence of Korea Institute of Science and Technology.

CROSS-REFERENCE TO RELATED APPLICATION

This application claims priority to Korean Patent Application No. 10-2014-0149941, filed on Oct. 31, 2014, and all the benefits accruing therefrom under 35 U.S.C. §119, the contents of which in its entirety are herein incorporated by reference

BACKGROUND

1. Field

The present disclosure relates to lignin microcapsules and a method for preparing the same. More particularly, the present disclosure relates to lignin microcapsules having a micro/nano-structure and a method for preparing the same.

2. Description of the Related Art

Lignin is a natural polymeric compound and a fat-soluble phenol polymer present at the cell walls of lignified plants, such as conifers or broad-leaved trees. Lignin is not amenable to acid hydrolysis due to its characteristic amorphous structure and has a chemical structure in which constitutional units of $C_3$-$C_6$ phenylpropane groups are condensed through carbon-carbon or ether bonds. Recently, importance of a biomass as a raw material for bioenergy has been increased, and thus many studies have been conducted about controlling the lignin content in a biomass by introducing the characteristics of enzymes involved in biosynthesis of lignin and molecular biological technologies, fibrillation of lignin, and about encapsulation of lignin.

A self-healing or self-restoring system refers to a system designed to have properties with which some defects can be detected and restored spontaneously according to specific environments such as heat, electricity and light with no artificial operation. Among such systems, applications of a self-healing material using microcapsules have been suggested in Nature, 2001 by the professor White in University of Illinois—Urbana-Champaign (UIUC) (USA). Particularly, microcapsules are added to a polymer matrix, external force is applied to the polymer matrix so that the polymer matrix is damaged, the wall materials of capsules are broken around the damaged portion, and then the internal core materials (curing agent or matrix reinforcing material, or the like) are discharged so that the polymer matrix restores its original physical properties.

Carbon nanotubes have a graphene layer wound in a cylindrical shape. Carbon nanotubes have been given many attentions as a first-dimension nanomaterial applicable to various industrial fields by virtue of their electrical and mechanical properties. However, there are many limitations in applying carbon nanotubes due to strong cohesive force unique to nanomaterials. To solve such a problem, a non-covalent functionalization method using various types of dispersants, polymers, DNA, proteins, or the like has been suggested. Particularly, there have been conducted studies about stabilization and efficient control of the dispersive property of carbon nanotubes in the presence of a solvent by using lignin.

REFERENCES OF THE RELATED ART

Non-Patent Documents

Mariarosaria Tortora., et al., Biomacromolecular 15, 1634-1643 (2014)
S. R. White, et al., Nature 409, 794-797 (2001)
Olivier Rochez, et al., J Mater Sci 48 (14), 4962-4964 (2013)

SUMMARY

The present disclosure is directed to providing lignin microcapsules having high yield and an optimized capsule particle size, size distribution and release amount, as well as a method for preparing the same.

The present disclosure is also directed to providing lignin microcapsules having improved electrical properties through the addition of carbon nanotubes as core materials thereof, as well as a method for preparing the same.

In a general aspect, there are provided lignin microcapsules including lignin as a shell material and oil and/or a carbonaceous material as a core material.

According to an embodiment, the lignin microcapsules may have a size of 10 nm-1 μm.

According to another embodiment, the lignin microcapsules may release oil under hydrophobic atmosphere.

According to still another embodiment, the carbonaceous material may be carbon nanotubes.

According to still another embodiment, the carbon nanotubes may be dispersed carbon nanotubes.

According to yet another embodiment, the lignin microcapsules may release carbon nanotubes under hydrophobic atmosphere.

In another general aspect, there is provided a method for preparing lignin microcapsules, including forming an oil-in-water (O/W) emulsion containing lignin, oil and water and carrying out polymerization to obtain lignin microcapsules.

According to an embodiment, it is possible to carry out interfacial polymerization of lignin in an oil-in-water (O/W) emulsion containing oil and water.

According to another embodiment, the interfacial polymerization may be carried out by ultrasonic polymerization.

According to still another embodiment, the ultrasonic polymerization may be carried out through an ultrasonic polymerization energy of 26-91 W.

According to still another embodiment, the ultrasonic polymerization may be carried out for 40-90 seconds.

According to still another embodiment, lignin may be used in a concentration of 5-20 wt %.

According to still another embodiment, the ratio of lignin: oil may be in a range of 5:1 to 20:1

According to still another embodiment, the emulsion may further include a carbonaceous material.

According to still another embodiment, the method may include forming oil in which a carbonaceous material is dispersed; and adding lignin and water to the oil in which the carbonaceous material is dispersed to form an oil-in-water (O/W) emulsion.

According to yet another embodiment, the carbonaceous material may be carbon nanotubes.

The lignin microcapsules disclosed herein provides the following effects.

First, the lignin microcapsules disclosed herein include a phenol structure in which lignin realizes antibacterial property and thus can be formed to have antibacterial property. Thus, the lignin microcapsules can be used as an additive in composite materials.

Second, the lignin microcapsules can be formed to allow release of their core materials which may include a material having high dispersibility, such as oil, and thus can be used as a dispersion stabilizer for carbon nanotubes.

Third, according to an embodiment, there is provided a condition by which the specific size of lignin microcapsules and/or release amount of core materials can be optimized. Therefore, by using the condition, it is possible to obtain nano-sized lignin microcapsules having a size and/or release amount of core materials suitable for a specific circumstance, and to fabricate nanofibers or nanowebs therefrom.

Fourth, the lignin-carbon nanotube microcapsules disclosed herein include carbon nanotubes having excellent self-restoring property as a core material. Therefore, when fabricating nanofibers or nanowebs including the lignin-carbon nanotube microcapsules, it is possible to allow the nanofibers or nanowebs to release carbon nanotubes under a specific atmosphere so that they may be used as medical materials, such as wound-restoring carbon nanofibers or hydrophobic drug delivery systems that restore a wound site, such as the dermis.

DETAILED DESCRIPTION

Exemplary embodiments now will be described more fully hereinafter so that the present disclosure will be thorough and complete, and will fully convey the scope of the present disclosure to those skilled in the art.

Hereinafter, exemplary embodiments will be described for the illustrative purposes only with reference to the accompanying drawings, in which exemplary embodiments are shown. The technical spirit, constitution and application of the present disclosure may, however, be embodied in many different forms and should not be construed as limited to the exemplary embodiments set forth therein.

As used herein, the term 'carbonaceous material' is used to cover its broadest concept including all of carbon-based materials, such as graphite, carbon nanotubes, or the like.

As used herein, the term 'carbon nanotubes' means a material having a cylindrical shape through the interconnection of hexagons of six carbon atoms.

As used herein, the term 'microcapsules' means a fine container and is used to cover its broadest concept including all of fine containers or particles in which a desired material is received without any limitation in particle size, such as several nanometers (nm), micrometers (μm), or the like.

As used herein, the term lignin microcapsules' means microcapsules including lignin as a shell material.

As used herein, the term lignin-carbonaceous material microcapsules' means including lignin as a shell material in combination with a carbonaceous material as a core material.

As used herein, the term lignin-carbon nanotube microcapsules' means including lignin as a shell material in combination with carbon nanotubes as a core material.

Hereinafter, exemplary embodiments of the present disclosure will be explained in detail.

Lignin Microcapsules and Method for Preparing the Same

The method for preparing lignin microcapsules according to an embodiment may include carrying out interfacial polymerization of lignin with an oil-in-water (O/W) emulsion containing oil and water.

Figure 1:
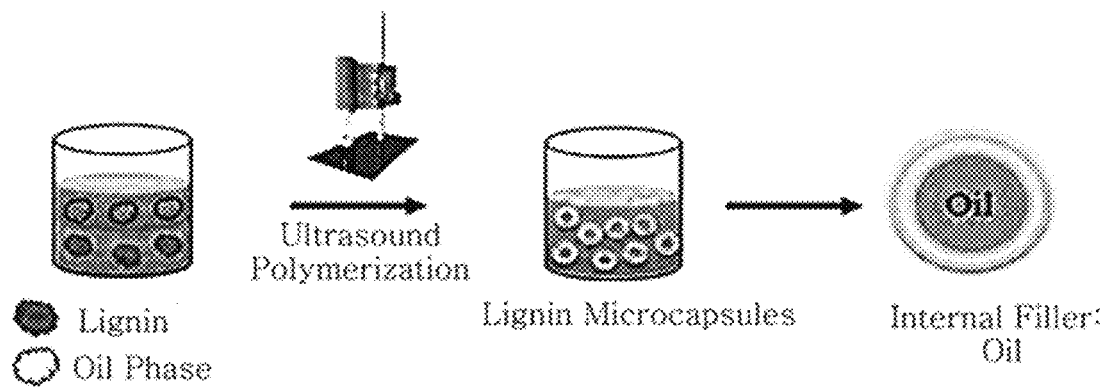
FIG. 1 is a schematic view illustrating the method for preparing lignin microcapsules according to an embodiment.

FIG. 1 is a schematic view illustrating the method for preparing lignin microcapsules according to an embodiment.

Referring to FIG. 1, lignin is added to a reactor containing oil and water. Herein, water is a polar material and oil is a non-polar material, and thus they are not mixed with each other but form an oil-in-water (O/W) emulsion. The lignin added to the reactor may exist in an aqueous solution (water) phase.

Emulsion polymerization is allowed when two liquids each having hydrophilic property and hydrophobic property have a certain ratio. Therefore, it is possible to form the lignin microcapsules according to an embodiment through the emulsion polymerization using hydrophilic lignin and hydrophobic oil.

According to an embodiment, the interfacial polymerization may be carried out by ultrasonic polymerization. Ultrasonic waves have an effect of improving the characteristics or enhancing the reaction rate in various chemical reactions, such as organic or inorganic reactions and polymerization. When carrying out ultrasonic polymerization, ultrasonic waves for irradiation generate and propagate air bubbles on the solution due to ultrasonic cavitation and cleave the long chain of a polymer subjected to polymerization, thereby contributing to production of nanoparticles.

According to another embodiment, when carrying out ultrasonic polymerization after lignin is introduced to a reactor containing water/oil and an emulsion is formed, lignin molecules present in the solution are bound with each other to form covalent bonds, resulting in production of circular microcapsules. Herein, ultrasonic polymerization generates strong air bubbles in the aqueous solution to form microcapsules stably in the form of small droplets and allows dispersion of microcapsules in the aqueous solution, thereby forming an emulsion. In addition, covalent bonds are formed between hydroxyl (—OH) groups and peroxide ($HO_2$—) groups of lignin, thereby contributing to production of microcapsules including lignin as a shell material. Herein, lignin forms covalent bonds through the interfacial polymerization at the interface between water and oil, resulting in production of microcapsules including oil as a core material in combination with lignin as a shell material.

According to still another embodiment, the lignin microcapsules obtained from the ultrasonic polymerization may have a size of 10 nm-1 μm.

According to still another embodiment, in the ultrasonic polymerization, the ultrasonic polymerization energy and/or ultrasonic polymerization time may be varied to obtain lignin microcapsules having different sizes and different release amounts of core materials.

According to still another embodiment, the ultrasonic polymerization may be carried out for 40-90 seconds. In addition, the ultrasonic polymerization may be carried out through an ultrasonic polymerization energy ranging from 26 W to 91 W.

According to still another embodiment, the concentration of lignin and/or ratio of lignin/oil may be varied to obtain lignin microcapsules having different sizes and different release amounts of core materials.

According to still another embodiment, the ratio of lignin/oil may be in a range of 5:1 to 20:1. In addition, lignin may be used in an amount of 5-20 wt %.

The lignin microcapsules according to an embodiment are formed by covalent bonds through ultrasonic polymerization of lignin at the interface between oil and water present in a water/oil emulsion. As a result, it is possible to obtain lignin microcapsules including lignin as a shell material and oil as a core material.

In addition, since the lignin microcapsules include a core material, when the shell material is cracked by a change in external conditions, for example under hydrophobic atmosphere, the core material may be released. When the core material is oil, oil may be released from the lignin microcapsules. According to an embodiment, the lignin microcapsules may react with a material containing a hydrophobic group, such as a surfactant, e.g. sodium dodecyl sulfate (SDS), sodium dodecylbenzene sulfonate (SDBS), or the like, thereby forming cracks on the shell material. As a result, oil may be released from the lignin microcapsules through the formed cracks.

Particularly, it is possible to use a surfactant having both hydrophilic property and hydrophobic property to allow the core material to be released from the lignin microcapsules according to an embodiment. When using such a surfactant, the hydrophilic groups of surfactant react with the hydrophilic lignin shell material to weaken the shell material, thereby allowing generation of cracks on the lignin shell material. Therefore, the hydrophobic core material may be released through the cracks generated on the lignin shell material, while the hydrophobic groups of surfactant and the hydrophobic core material are in a phase equilibrium state so that the core material may be released out easily from the lignin microcapsules.

The lignin microcapsules according to an embodiment have excellent dispersing capability and thus may contribute to improvement of the dispersibility of the other materials. Particularly, the lignin microcapsules according to an embodiment include lignin containing a hydrophilic group such as OH— group as a shell material. Therefore, for example, when forming an aqueous solution including carbon nanotubes and the lignin microcapsules according to an embodiment, the hydrophilic groups of carbon nanotubes and those of lignin are bound with each other to improve the dispersibility of carbon nanotubes in the aqueous solution.

In addition, the lignin microcapsules according to an embodiment may have antibacterial property. Lignin has both a phenol group and ether group, wherein the phenol group is known as a typical molecular structure realizing antibacterial property. The antibacterial property of lignin may be realized by applying external force to the microbial cell membranes containing lignin to break or decompose the cell membranes, and then allowing the contents inside lignin to be released from the broken cell membranes so that they destruct external bacteria. In addition, some types of lignin have a specific microstructure or excellent adsorption property, and thus they allow adsorption of organic contaminants and microorganisms. Therefore, it is possible to realize antibacterial property while the contaminants present on the contact surface are subjected to bio-degradation. In this manner, the lignin-containing lignin microcapsules may realize antibacterial property.

Additionally, the method for preparing the lignin microcapsules according to an embodiment suggests a condition optimized for forming nano-sized microcapsules. Further, the method for preparing the lignin microcapsules disclosed herein suggests a condition optimized for forming lignin microcapsules having an optimized release amount of core material. In this manner, it is possible to obtain lignin microcapsules having a size and release amount of core material optimized for nanofibers or nanowebs.

Lignin-Carbonaceous Material Microcapsules and Method for Preparing the Same

The method for preparing lignin-carbonaceous material microcapsules according to an embodiment may include: forming oil in which a carbonaceous material is dispersed; adding lignin and water to the oil in which the carbonaceous material is dispersed to form an oil-in-water (O/W) emulsion; and carrying out interfacial polymerization of the lignin and oil-in-water (O/W) emulsion.

Hereinafter, each operation will be described. For convenience, the carbonaceous material is exemplified by carbon nanotubes. However, carbonaceous materials other than carbon nanotubes may also be used suitably according to an embodiment.

Figure 9:
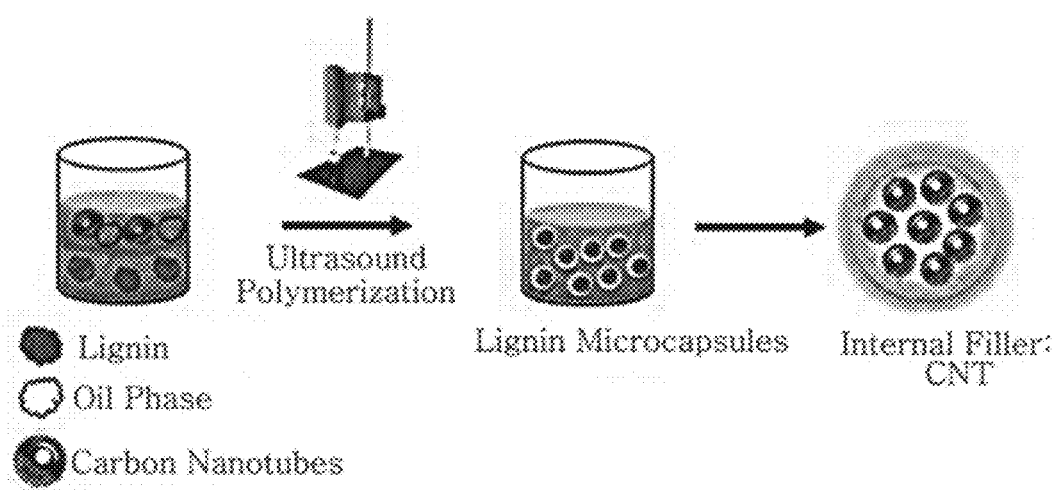
FIG. 9 is a schematic view illustrating the method for preparing lignin-carbonaceous material microcapsules according to an embodiment.

FIG. 9 is a schematic view illustrating the method for preparing lignin-carbonaceous material microcapsules according to an embodiment.

Referring to FIG. 9, oil containing a carbonaceous material dispersed therein is formed. Herein, since both the carbonaceous material and oil are non-polar, the carbonaceous material may be dispersed homogeneously in oil.

According to an embodiment, the oil may be olive oil, or the like, and the carbonaceous material may be carbon nanotubes, graphite, or the like.

Then, lignin and water are added to the oil containing the carbonaceous material dispersed therein to form an oil-in-water (O/W) emulsion, and interfacial polymerization of the oil-in-water (O/W) emulsion and lignin may be carried out. Herein, since water is a polar material, oil is a non-polar material and they are not miscible with each other, it is possible to form an oil-in-water (O/W) emulsion, wherein lignin is present in the aqueous solution phase.

According to an embodiment, the interfacial polymerization of lignin and the oil-in-water (O/W) emulsion may be carried out by ultrasonic polymerization. Herein, ultrasonic polymerization generates strong air bubbles in the aqueous solution phase and allows formation of covalent bonds between lignin molecules, resulting in production of circular lignin-carbonaceous material microcapsules.

According to an embodiment, in the ultrasonic polymerization, the ultrasonic polymerization energy, ultrasonic polymerization time, lignin concentration or the ratio of lignin/oil may be varied to obtain lignin-carbonaceous material microcapsules having different sizes and different release amounts of core material. In this case, the same or similar description as in the method for preparing lignin microcapsules is also applied, and thus detailed description thereof will be omitted.

In this manner, it is possible to obtain lignin-carbonaceous material microcapsules including lignin as a shell material in combination with oil carbonaceous material as a core material.

In addition, since the lignin microcapsules include the carbonaceous material dispersed in oil, the shell material may be cracked by a change in external conditions, for example under hydrophobic atmosphere, so that the core material, i.e., the carbonaceous material dispersed in oil may be released from the microcapsules.

According to an embodiment, when the carbonaceous material is carbon nanotubes, carbon nanotubes dispersed in oil may be released from the lignin-carbonaceous material microcapsules.

Meanwhile, when forming lignin-carbonaceous material microcapsules including lignin and carbon nanotubes as shell materials in combination with oil as a core material, the carbon nanotubes dispersed therein offset the crosslinking capability of lignin during the polymerization of emulsion using ultrasonication. Thus, it is not easy to form lignin-carbonaceous material microcapsules.

On the contrary, the lignin-carbonaceous material microcapsules according to an embodiment is formed to have a carbonaceous material as a core material in such a manner that a carbonaceous material, including carbon nanotubes, is not a shell material but is dispersed in an organic phase, such as oil, and then lignin is added thereto. Therefore, since the carbonaceous material, such as carbon nanotubes, may not offset the crosslinking of lignin, it is easy to form crosslinking of lignin by using ultrasonic waves during the preparation of the lignin-carbonaceous material microcapsules according to an embodiment. In addition, the obtained lignin-carbonaceous material microcapsules may contribute to the maintenance of dispersibility of carbon nanotubes in an oil phase.

The lignin-carbonaceous material microcapsules according to an embodiment include a carbonaceous material having high self-restoring property as a core material. Therefore, when fabricating nanofibers or nanowebs containing the lignin-carbonaceous material microcapsules, it is possible to allow the nanofibers or nanowebs to release carbon nanotubes under a specific atmosphere so that they may be used as medical materials, such as wound-restoring carbon nanofibers or hydrophobic drug delivery systems that restore a wound site, such as the dermis.

The examples and experiments will now be described. The following examples and experiments are for illustrative purposes only and not intended to limit the scope of the present disclosure.

EXAMPLE 1

Preparation of Lignin Microcapsules Using Ultrasonic Polymerization

First, 0.05 g of lignin and 1 ml of distilled water are agitated with 100 µl of olive oil, and then subjected to sonication to obtain microcapsules. Herein, the ratio of lignin/oil is set to 10:1. In addition, ultrasonic polymerization energy and ultrasonic polymerization time are set to 91 W and 80 seconds, respectively. The lignin microcapsules are prepared with a lignin concentration of 5 wt %.

TEST EXAMPLE 1-1

Determination of Size and Appearance of Lignin Microcapsules

The lignin microcapsules obtained from Example 1 are analyzed by a confocal microscope, electronic microscope and transmission electron microscope (TEM). The lignin microcapsules are observed in terms of their release of core material.

Figure 2A:
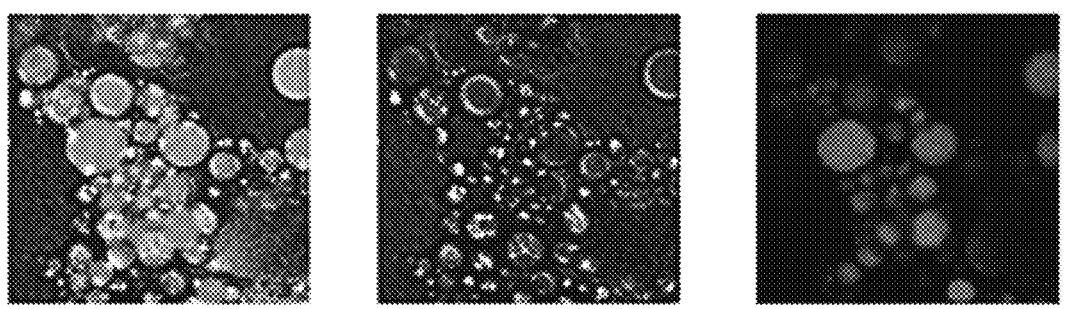
FIGS. 2a-2c show a confocal microscopic image of the lignin microcapsules obtained according to an embodiment, scanning electron microscopic (SEM) image thereof and transmission electron microscopic (TEM) image thereof, respectively.
Figure 2B:
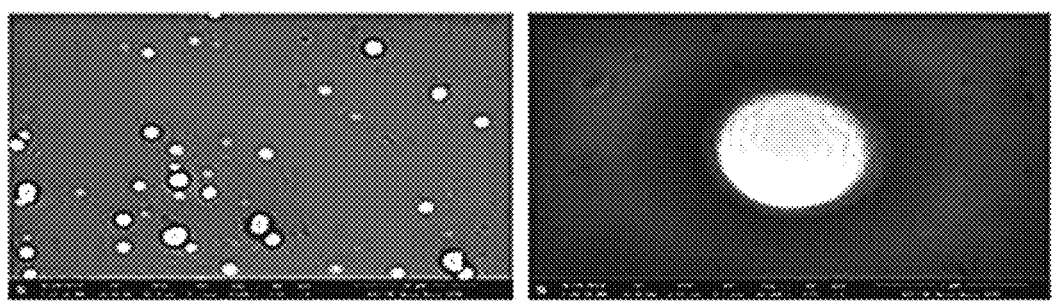
Figure 2C:
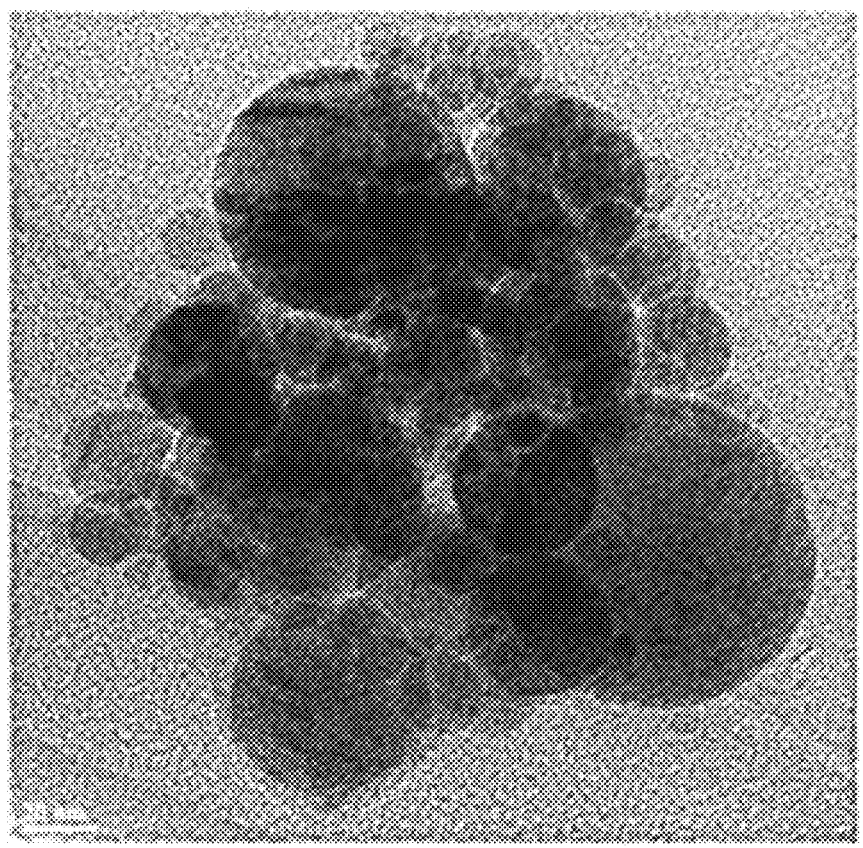

FIGS. 2a-2c show a confocal microscopic image of the lignin microcapsules obtained according to an embodiment, scanning electron microscopic (SEM) image thereof and transmission electron microscopic (TEM) image thereof, respectively. Particularly, FIG. 2a is a confocal microscopic image of the microcapsules obtained by using a fluorescent material, Coumarin 6, in olive oil as a core material.

The confocal microscopic image of FIG. 2a allows determination of the overall distribution of microcapsules. The SEM and TEM images of FIG. 2b and FIG. 2c allow determination of precise size distribution of microcapsules.

Referring to FIG. 2a and FIG. 2b, it can be seen that lignin microcapsules having a different diameter of about 2-4 µm are formed to have a different distribution in aqueous solution. Particularly, it can be seen from FIG. 2a that olive oil is filled into the lignin microcapsules.

It can be seen from the image of FIG. 2c showing the lignin microcapsules obtained according to Example 1 that lignin microcapsules having a different diameter of about 10 nm-1 µm are formed.

TEST EXAMPLE 1-2

Determination of Behavior of Releasing Core Material from Lignin Microcapsules The lignin shell materials of the lignin microcapsules obtained according to Example 1 are weakened by using a surfactant including SDBS or SDS so that the core materials having a hydrophobic group may be released. Herein, the hydrophilic groups of surfactant react with the lignin shell materials to generate cracks on the shell materials of lignin microcapsules, and the hydrophobic core materials are released from the lignin microcapsules through the shell materials.

Figure 3:
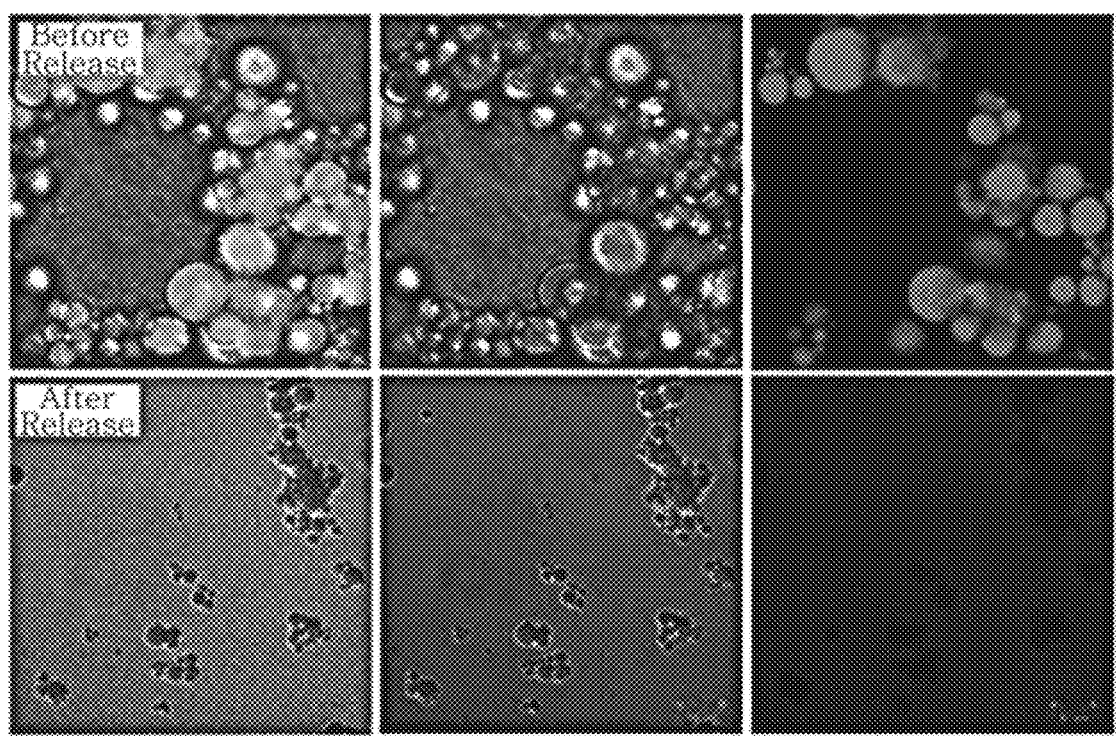
FIG. 3 is a photographic image illustrating the release behavior of the lignin microcapsules according to an embodiment.

FIG. 3 is a confocal microscopic image illustrating the release behavior of the lignin microcapsules according to an embodiment. Referring to FIG. 3, it can be seen from the image taken after the release of lignin microcapsules that the solution containing the lignin microcapsules has a fluorescent color and the lignin microcapsules from which oil is released have a gray color. This suggests that the lignin microcapsules release olive oil under hydrophobic atmosphere.

TEST EXAMPLE 1-3

Determination of Dispersibility of Carbon Nanotubes in Lignin

Figure 4A:
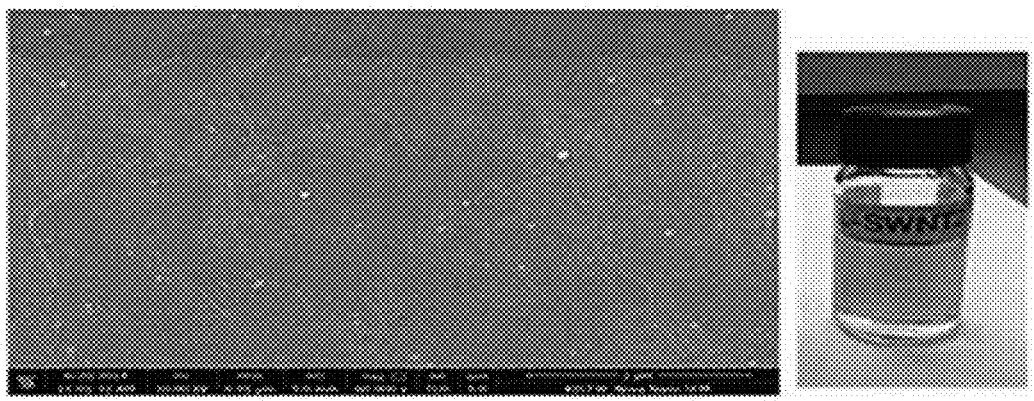
FIGS. 4a-4c show photographic images illustrating high dispersibility of carbon nanotubes when using the lignin microcapsules according to an embodiment.
Figure 4B:
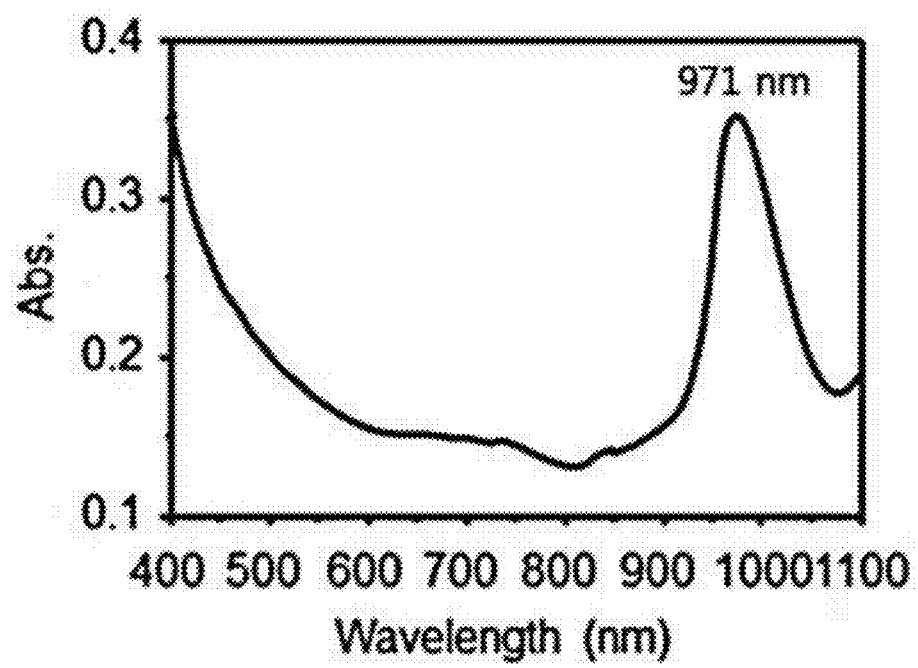
Figure 4C:
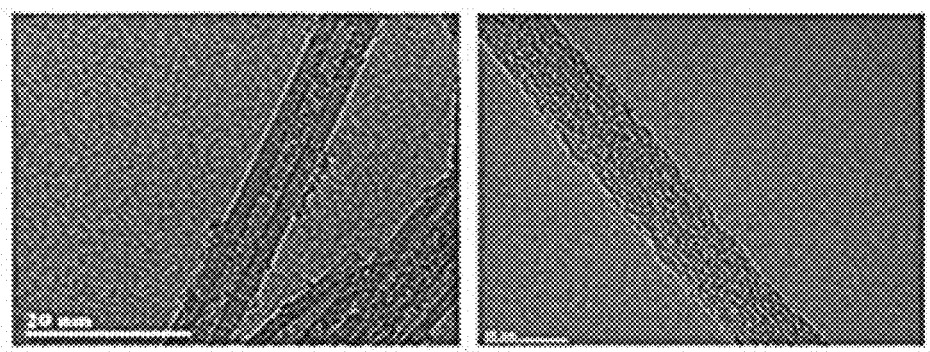
Figure 4C:
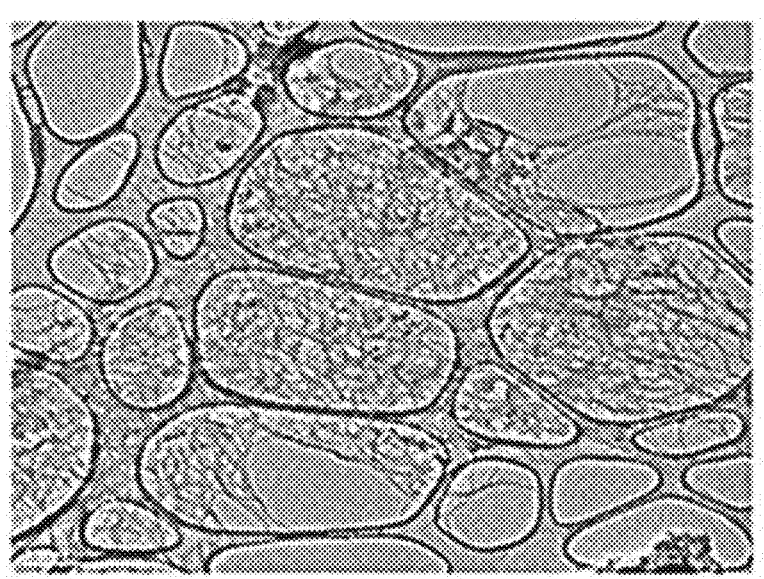

To determine the dispersibility of carbon nanotubes using the lignin microcapsules obtained according to Example 1, observation is carried out by the naked eyes, electron microscopes (SEM, TEM) and UV-Vis spectrometry, and the results are shown in FIGS. 4a-4c.

Particularly, 7.5 mg of lignin microcapsules and 5 mg of carbon nanotubes are added to 50 ml of distilled water, and then the resultant mixture is subjected to ultrasonication to obtain an aqueous dispersion of carbon nanotubes. More particularly, the ultrasonication is carried out by treating the aqueous dispersion of carbon nanotubes under 52 W at 4° C. for 1 hour, followed by treatment in a centrifugal system under 240,000 G (49,700 rpm) 4° C. for 1 hour. Then, only 70% of the supernatant of the aqueous dispersion of carbon nanotubes is taken and observed.

Referring to FIGS. 4a-4c, the carbon nanotubes are not agglomerated but distributed homogeneously in the aqueous lignin solution. In general, the dispersion stability of carbon nanotubes in a solution is not high. However, in the presence of aqueous lignin solution, since lignin contains hydrophilic —OH groups, carbon nanotubes react with —OH groups of lignin so that the carbon nanotubes may be distributed well. Thus, as shown in FIGS. 4a-4c, carbon nanotubes are not agglomerated but distributed in the aqueous lignin solution.

EXAMPLE 2

Preparation of Lignin Microcapsules Having Different Lignin Concentrations

First, 0.05 g of lignin and 1 ml of distilled water are agitated with 100 μl of olive oil, and then subjected to sonication to obtain microcapsules. Herein, the ratio of lignin/oil is set to 10:1. In addition, ultrasonic polymerization energy and ultrasonic polymerization time are set to 91 W and 80 seconds, respectively. The lignin microcapsules are prepared with a lignin concentration of 5, 10, 15 or 20 wt % to provide Samples 1-4.

TEST EXAMPLE 2

Determination of Variations in Size and Core Material Release Amount of Lignin Microcapsules Depending on Lignin Concentration Samples 1-4 are determined for size distribution of microcapsules and release amount of core materials, and the results are shown in the following Table 1 and FIG. 5Sa-5c.

TABLE 1

| | Lignin concentration | Average diameter of lignin microcapsules | Diameter distribution of lignin microcapsules | Release amount of core materials (%) | | |
|---|---|---|---|---|---|---|
| | (wt %) | (nm) | (PDI) | 1 hr | 2 hr | 3 hr |
| Sample 1 | 5 | 416 | 0.511 | 88 | 96 | 99 |
| Sample 2 | 10 | 304 | 0.472 | 91 | 97 | 99 |
| Sample 3 | 15 | 186 | 0.163 | 76 | 96 | 99 |
| Sample 4 | 20 | 265 | 0.402 | 88 | 95 | 99 |

Figure 5A:
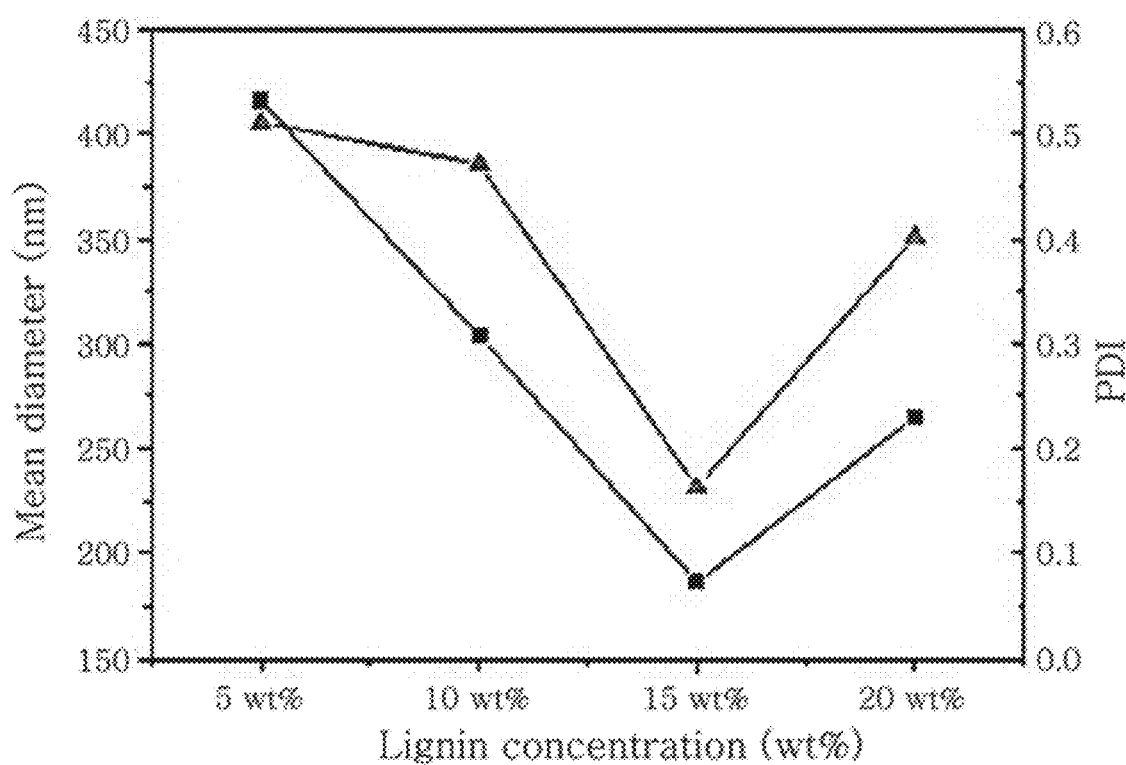
FIGS. 5a-5c show a graph illustrating the sizes of the lignin microcapsules obtained by using different contents of lignin according to an embodiment, an SEM image of the lignin microcapsules at a lignin concentration of 5%, and a graph illustrating the release amounts of core materials in the lignin microcapsules obtained by using different contents of lignin according to an embodiment, respectively.
Figure 5B:
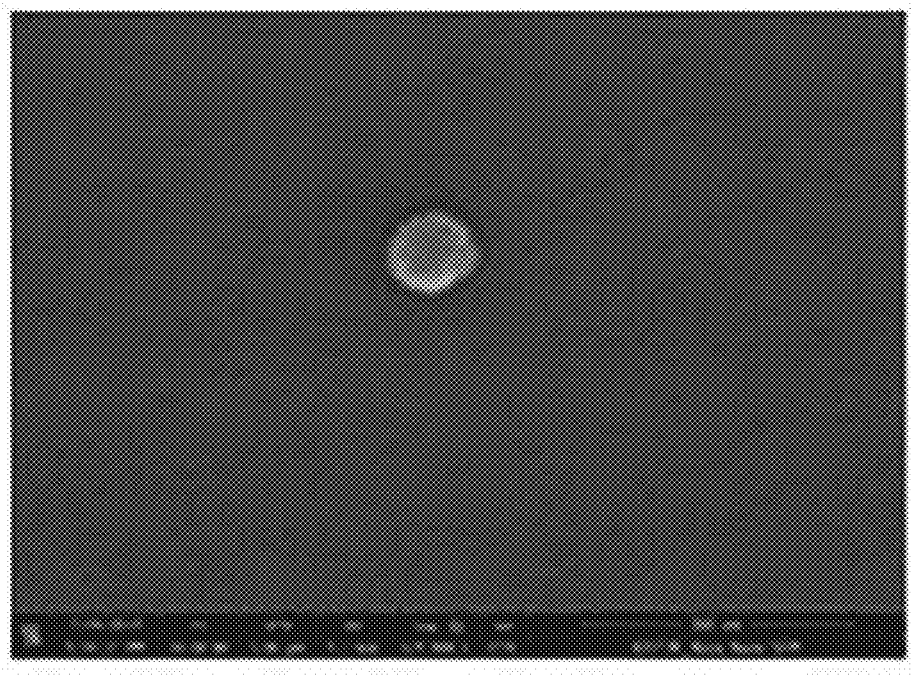
Figure 5C:
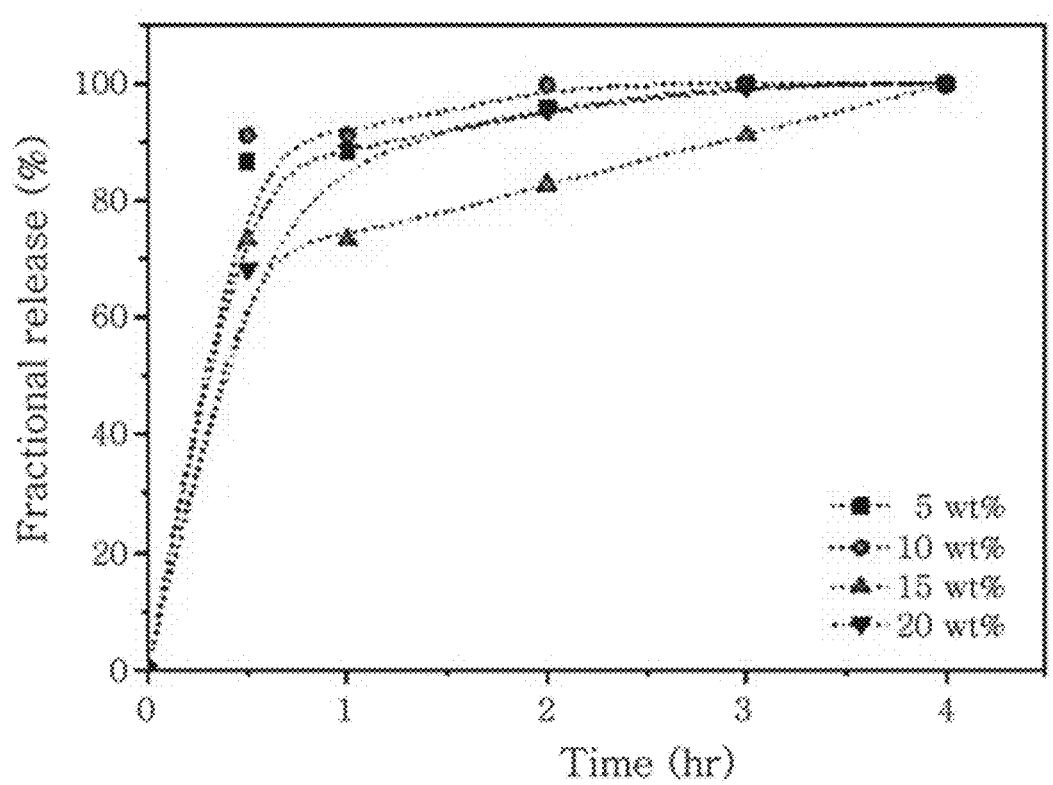

FIG. 5a shows a graph illustrating the sizes of the lignin microcapsule samples 1-4 obtained by using a different concentration of lignin of 5, 10, 15 or 20% according to Example 2, as determined by using zeta potential. Referring to FIG. 5a and Table 1, it can be seen that lignin microcapsules having an average size of about 170-430 nm are formed depending on lignin concentration. In addition, FIG. 5b shows an SEM image of sample 1 and demonstrates formation of spherical microcapsules. FIG. 5c shows a graph illustrating the release amounts of core materials in samples 1-4. It can be seen that sample 2 having a lignin concentration of 10% provides the highest release amount of core materials after the lapse of about 1 hour. It is though that this is because a lignin concentration greater than 10% shows an excessively large thickness of a shell material, thereby making it difficult to generate cracks on the shell material and to release the core material.

EXAMPLE 3

Preparation of Lignin Microcapsules Having Different Ratio of Lignin/Oil

First, 0.05 g of lignin and 1 ml of distilled water are agitated with 100 μl of olive oil, and then subjected to sonication to obtain microcapsules. Herein, the lignin concentration is set to 10 wt %. In addition, ultrasonic polymerization energy and ultrasonic polymerization time are set to 91 W and 80 seconds, respectively. The lignin microcapsules are prepared with a ratio of lignin/oil of 1:1. 5:1, 10:1 or 20:1 to provide Samples 5-7.

TEST EXAMPLE 3

Determination of Variations in Size and Core Material Release Amount of Lignin Microcapsules Depending on Ratio of Lignin/Oil Samples 5-7 are determined for size distribution of microcapsules and release amount of core materials, and the results are shown in the following Table 2 and FIGS. 6a-6c.

TABLE 2

| | Ratio of Lignin/Oil (w/w) | Average diameter of lignin microcapsules (nm) | Diameter distribution of lignin microcapsules (PDI) | Release amount of core materials (%) | | |
|---|---|---|---|---|---|---|
| | | | | 1 hr | 2 hr | 3 hr |
| Sample 5 | 5:1 | 238 | 0.288 | 80 | 96 | 99 |
| Sample 6 | 10:1 | 186 | 0.163 | 76 | 96 | 99 |
| Sample 7 | 20:1 | 219 | 0.211 | 95 | 97 | 99 |

Figure 6A:
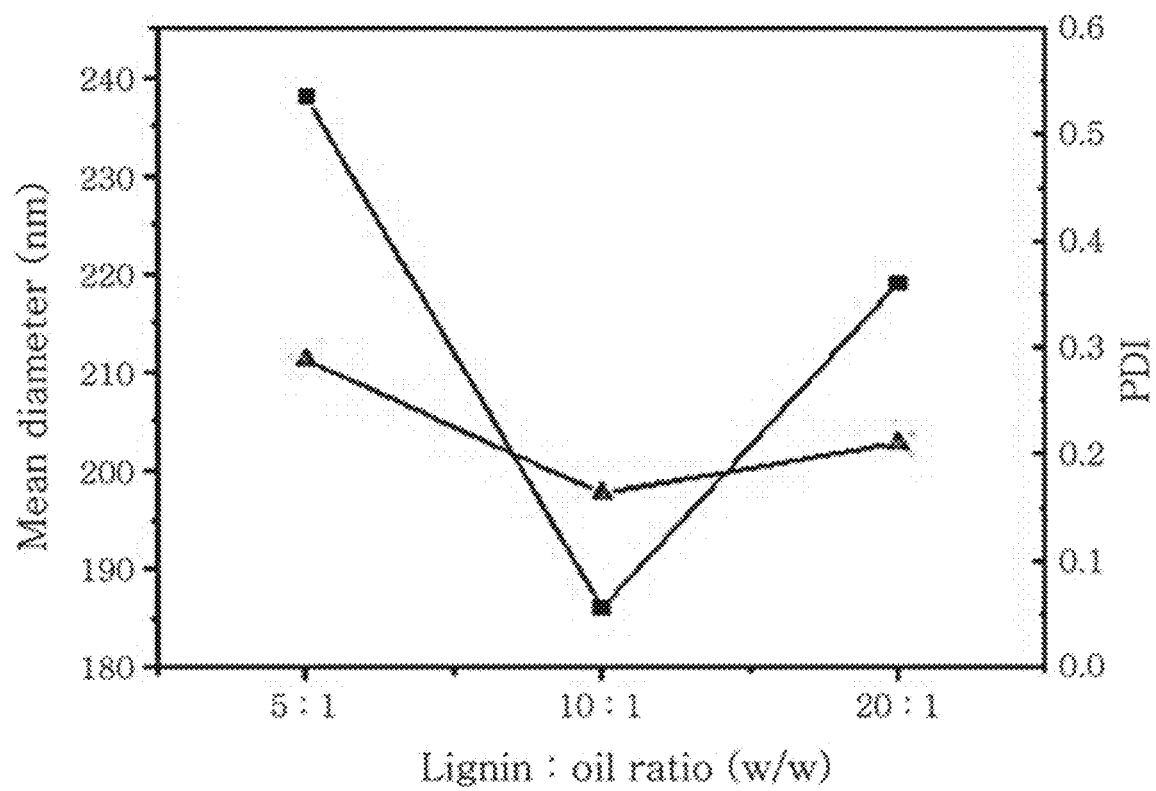
FIGS. 6a-6c show a graph illustrating the sizes of the lignin microcapsules obtained by using different ratios of lignin:oil according to an embodiment, an SEM image of the lignin microcapsules at a ratio of lignin:oil of 10:1, and a graph illustrating the release amounts of core materials in the lignin microcapsules obtained by using different ratios of lignin:oil according to an embodiment, respectively.

FIG. 6a shows a graph illustrating the diameters of the lignin microcapsule samples 5-7, as determined by using zeta potential. Referring to FIG. 6a and Table 2, it can be seen that lignin microcapsules having an average size of about 186-238 nm are formed depending on ratio of lignin/oil.

Figure 6B:
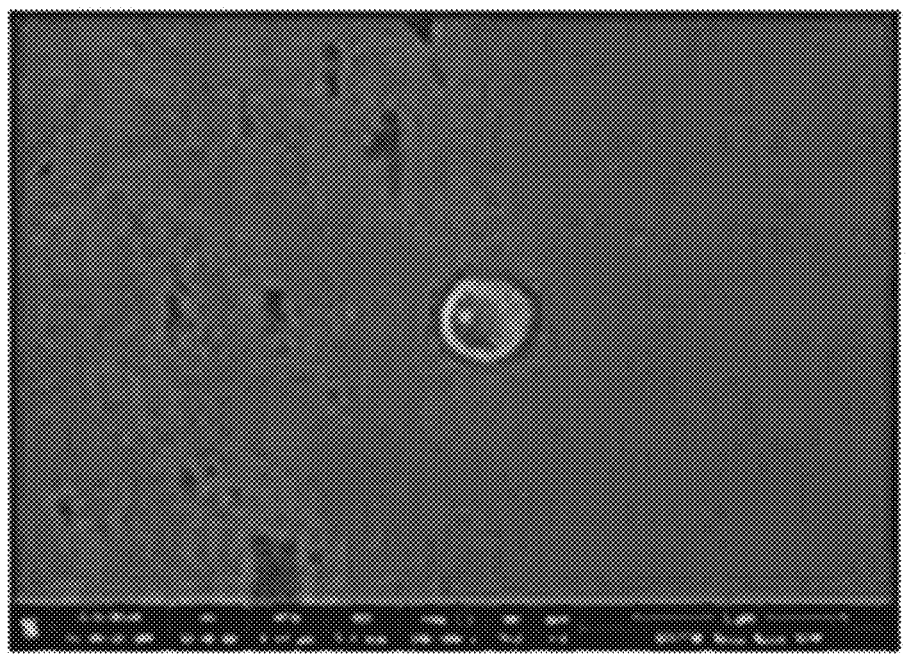

In addition, FIG. 6b shows an SEM image of sample 6 and demonstrates formation of spherical microcapsules.

Figure 6C:
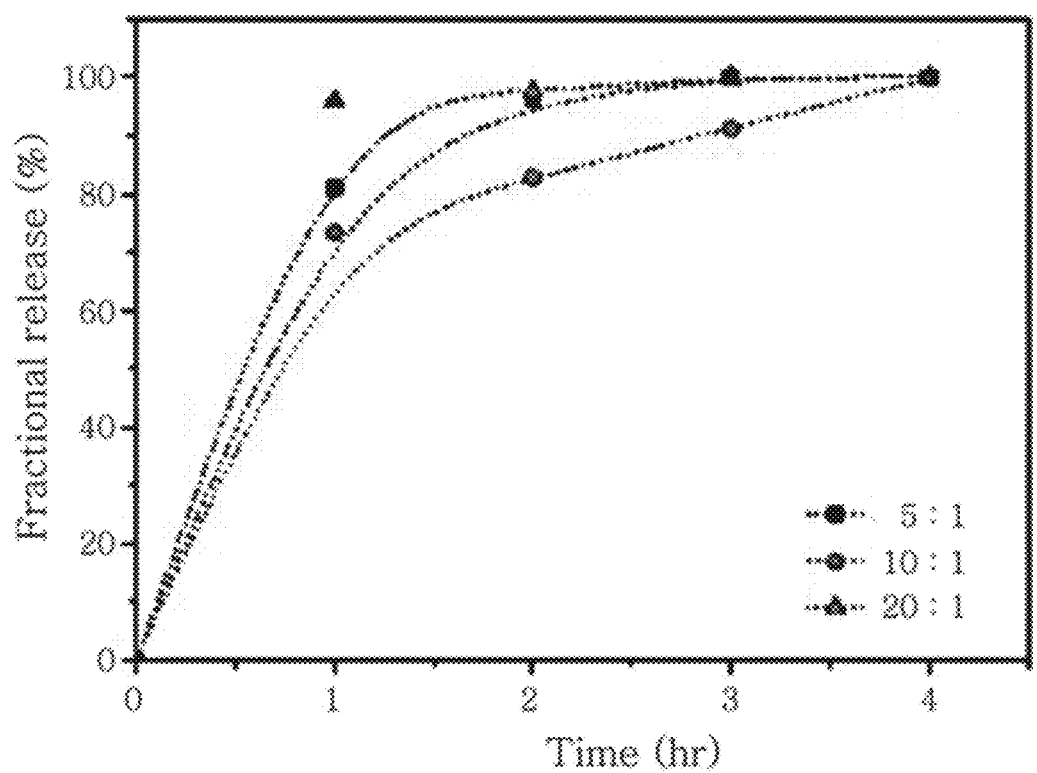

FIG. 6c shows a graph illustrating the release amounts of core materials in samples 5-7. It can be seen that sample 7 having a ratio of lignin/oil of 20:1 provides the highest release amount of core materials after the lapse of about 1 hour.

EXAMPLE 4

Preparation of Lignin Microcapsules Using Different Ultrasonic Polymerization Energy First, 0.05 g of lignin and 1 ml of distilled water are agitated with 100 μl of olive oil, and then subjected to sonication to obtain microcapsules. Herein, the lignin concentration is set to 10 wt %. In addition, a ratio of lignin/oil and ultrasonic polymerization time are set to 10:1 and 80 seconds, respectively. The lignin microcapsules are prepared by adjusting ultrasonic polymerization energy to 26 W, 52 W or 91 W to provide Samples 8-10.

TEST EXAMPLE 4

Determination of Variations in Size and Core Material Release Amount of Lignin Microcapsules Depending on Ultrasonic Polymerization Energy Samples 8-10 are determined for size distribution of microcapsules and release amount of core materials, and the results are shown in the following Table 3 and FIGS. 7a-7c.

TABLE 3

| | Ultrasonic polymerization energy (W) | Average diameter of lignin microcapsules (nm) | Release amount of core materials (%) | | |
|---|---|---|---|---|---|
| | | | 1 hr | 2 hr | 3 hr |
| Sample 8 | 26 | 262 | 80 | 97 | 99 |
| Sample 9 | 52 | 210 | 72 | 82 | 87 |
| Sample 10 | 91 | 186 | 95 | 96 | 99 |

Figure 7A:
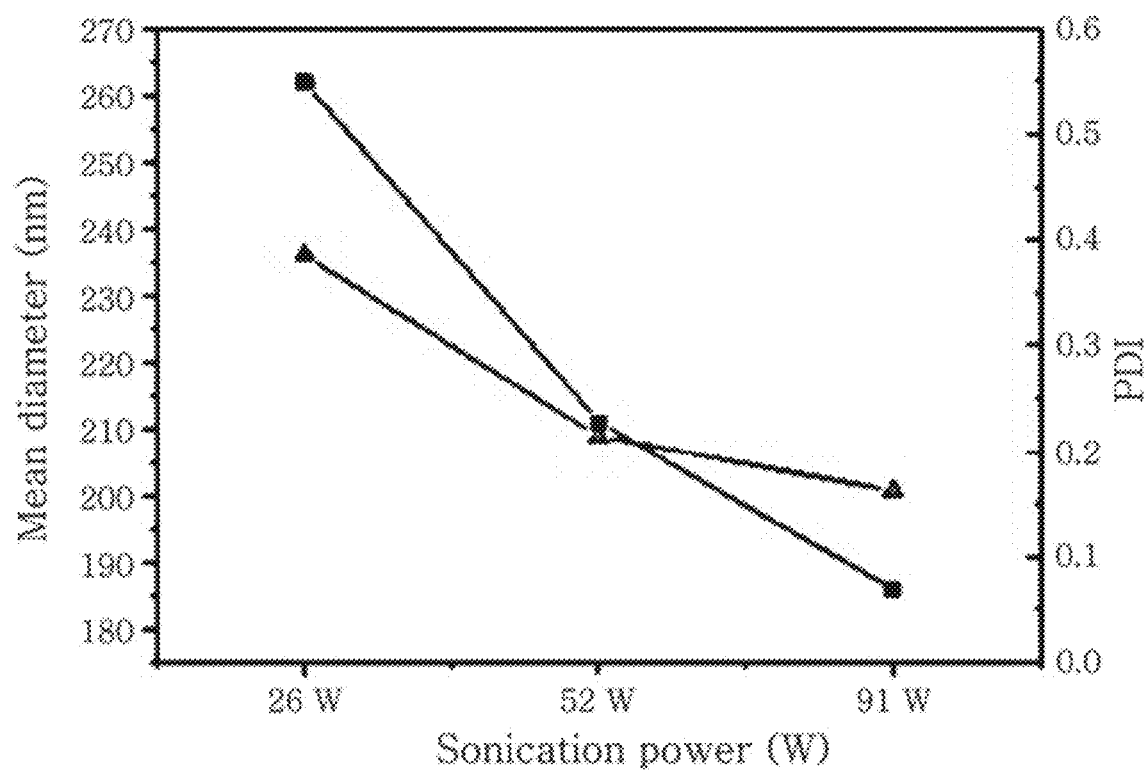
FIGS. 7a-7c show a graph illustrating the sizes of the lignin microcapsules obtained by using different ultrasonic polymerization energies according to an embodiment, an SEM image of the lignin microcapsules at an ultrasonic polymerization energy of 52 W, and a graph illustrating the release amounts of core materials in the lignin microcapsules obtained by using different ultrasonic energies according to an embodiment, respectively.
Figure 7B:
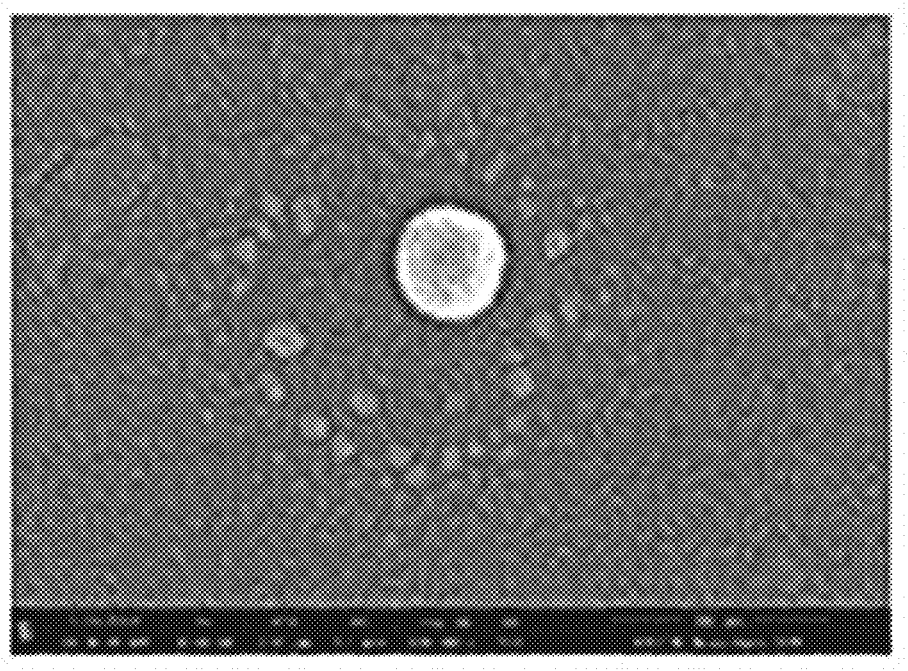

FIG. 7a shows a graph illustrating the diameters of the lignin microcapsule samples 8-10, as determined by using zeta potential. Referring to FIG. 7a and Table 3, it can be seen that lignin microcapsules having an average size of about 186-262 nm are formed depending on ultrasonic polymerization energy. In addition, FIG. 7b shows an SEM image of sample 9 and demonstrates formation of spherical microcapsules.

Figure 7C:
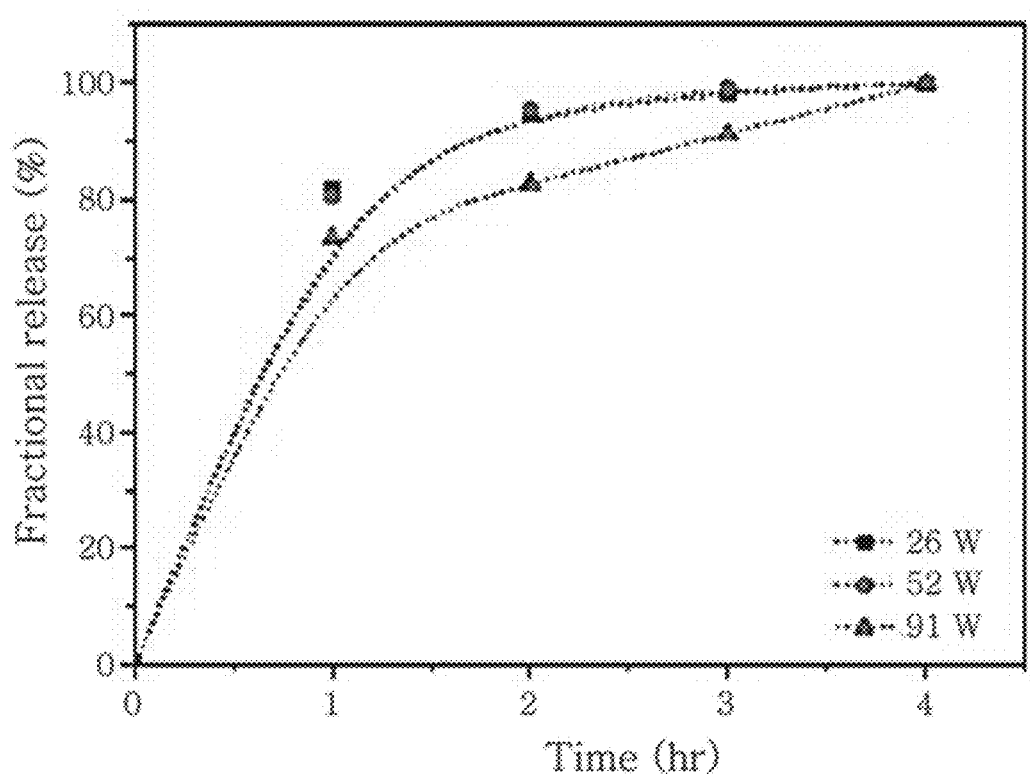

FIG. 7c shows a graph illustrating the release amounts of core materials in samples 8-10. It can be seen that sample 10 using an ultrasonic polymerization energy of 91 W provides the highest release amount of core materials after the lapse of about 1 hour.

EXAMPLE 5

Preparation of Lignin Microcapsules Using Different Ultrasonic Polymerization Time First, 0.05 g of lignin and 1 ml of distilled water are agitated with 100 μl of olive oil, and then subjected to sonication to obtain microcapsules. Herein, the lignin concentration is set to 10 wt %. In addition, a ratio of lignin/oil and ultrasonic polymerization energy are set to 10:1 and 91 W, respectively. The lignin microcapsules are prepared by adjusting ultrasonic polymerization time to 40, 80 or 90 seconds to provide Samples 11-13.

TEST EXAMPLE 5

Determination of Variations in Size and Core Material Release Amount of Lignin Microcapsules Depending on Ultrasonic Polymerization Time Samples 11-13 are determined for size distribution of microcapsules and release amount of core materials, and the results are shown in the following Table 4 and FIGS. 8a-8c.

TABLE 4

| | Ultrasonic polymerization time (sec) | Average diameter of lignin microcapsules (nm) | Diameter distribution of lignin microcapsules (PDI) | Release amount of core materials (%) | | |
|---|---|---|---|---|---|---|
| | | | | 1 hr | 2 hr | 3 hr |
| Sample 11 | 40 | 231 | 0.216 | 80 | 95 | 98 |
| Sample 12 | 80 | 186 | 0.163 | 73 | 83 | 91 |
| Sample 13 | 90 | 177 | 0.177 | 76 | 96 | 99 |

Figure 8A:
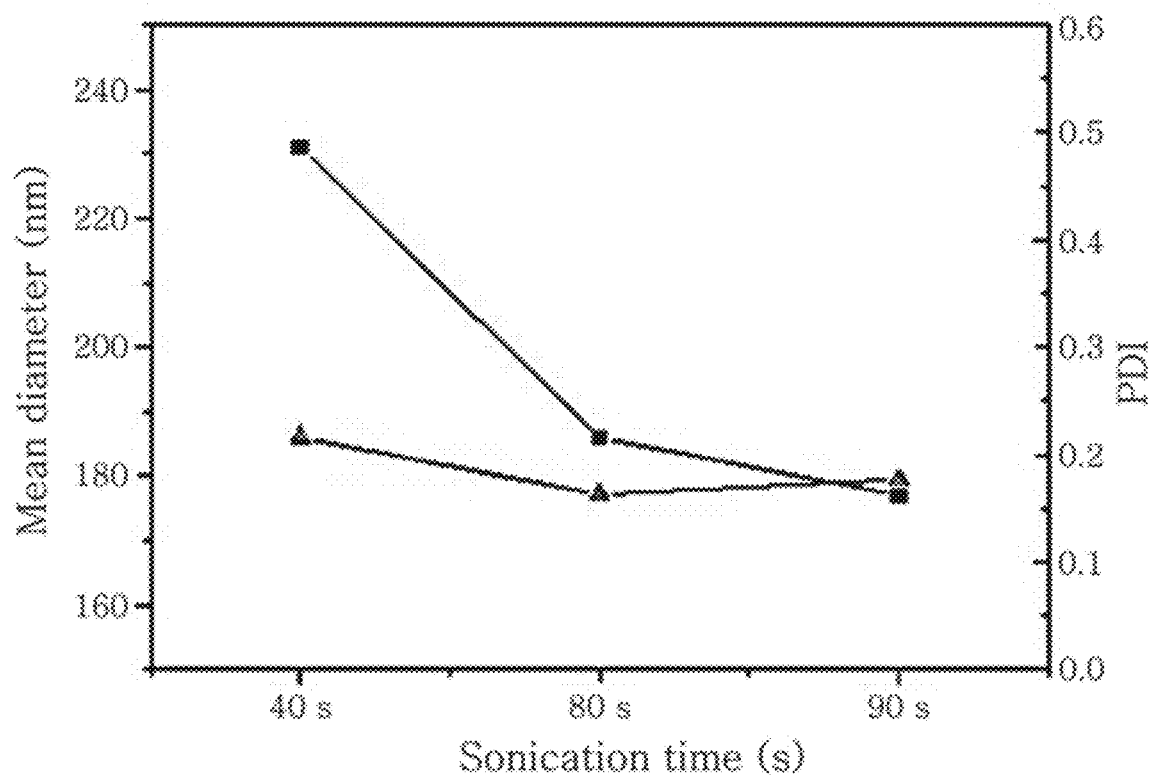
FIGS. 8a-8c show a graph illustrating the sizes of the lignin microcapsules obtained by using different ultrasonic polymerization treatment times according to an embodiment, an SEM image of the lignin microcapsules when the ultrasonic polymerization time is 80 seconds, and a graph illustrating the release amounts of core materials in the lignin microcapsules obtained by using different ultrasonic polymerization treatment times according to an embodiment, respectively.

FIG. 8a shows a graph illustrating the diameters of the lignin microcapsule samples 11-13, as determined by using zeta potential. Referring to FIG. 8a and Table 4, it can be seen that lignin microcapsules having an average size of about 177-231 nm are formed depending on ultrasonic polymerization time.

Figure 8B:

In addition, FIG. 8b shows an SEM image of sample 12 and demonstrates formation of spherical microcapsules.

Figure 8C:
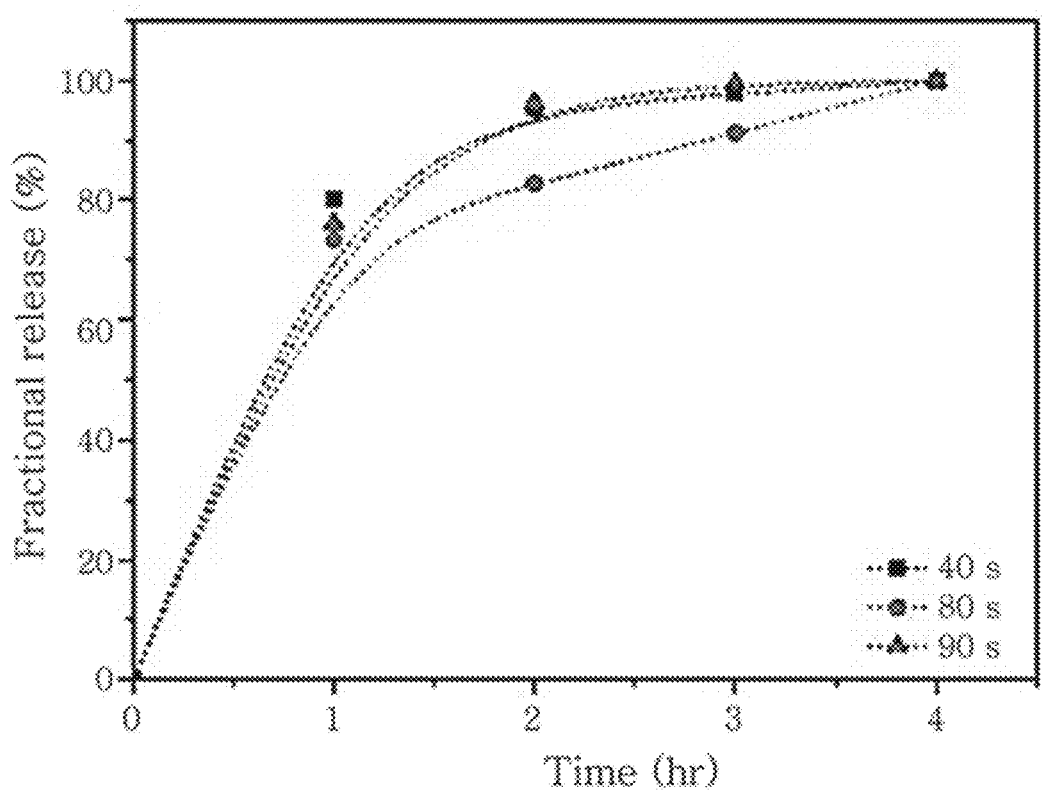

FIG. 8c shows a graph illustrating the release amounts of core materials in samples 11-13. It can be seen that sample 13 using an ultrasonic polymerization time of 90 seconds provides the highest release amount of core materials.

EXAMPLE 6

Preparation of Lignin-Carbon Nanotube Microcapsules

To obtain lignin microcapsules including carbon nanotubes therein, 100 mg of carbon nanotubes are dispersed in 100 μl of olive oil, and then a solution containing 0.15 g of lignin and 1 ml of distilled water is added thereto, followed by ultrasonic polymerization at 91 W for 80 seconds. Then, filtering is carried out by using a membrane filter with a size of 200 nm, followed by centrifugal separation and washing with water, thereby providing lignin-carbon nanotube microcapsules. Herein, during the test, lignin concentration is set to 15 wt % and a ratio of lignin/oil is set to 10:1. In addition, ultrasonic polymerization energy and time are set to 91 W and 80 seconds, respectively.

TEST EXAMPLE 6

Figure 10A:
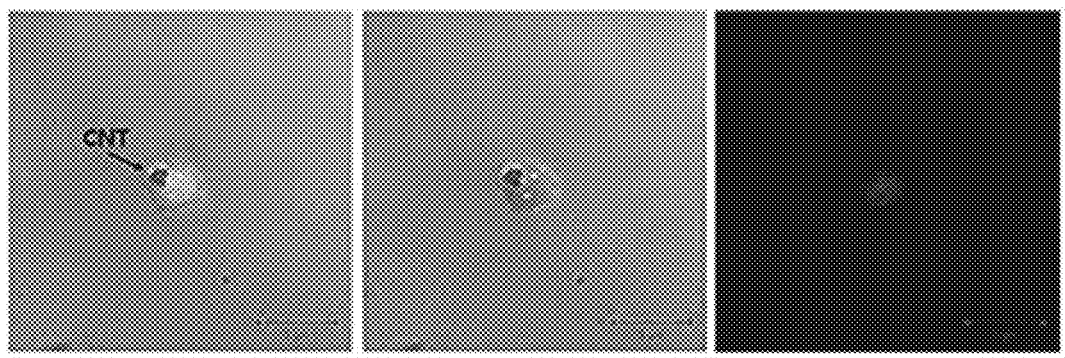
FIG. 10a and FIG. 10b each show the confocal microscopic images of the lignin-carbonaceous material microcapsules formed according to an embodiment.
Figure 10B:
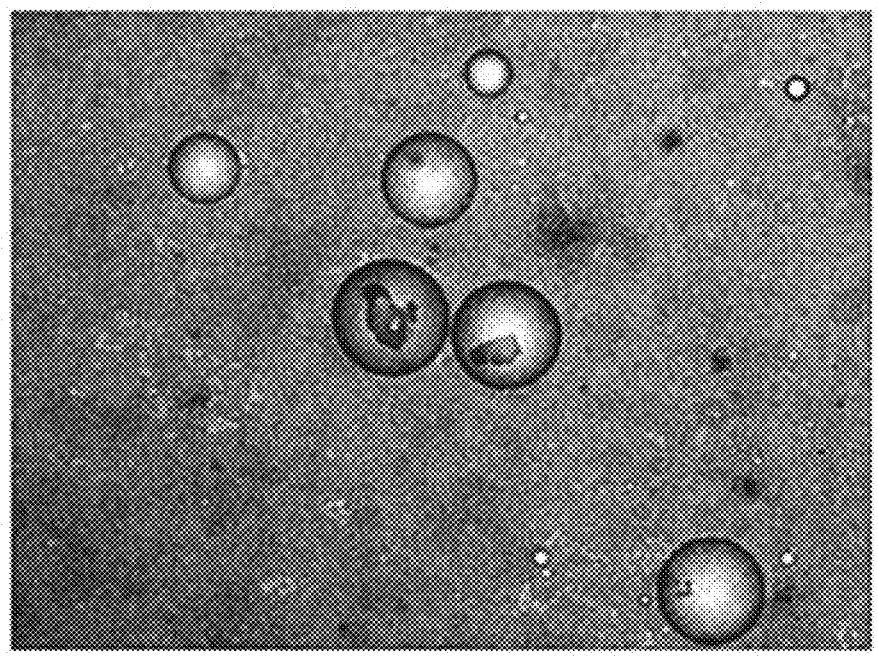

Determination of Size and Core Material Release Amount of Lignin-Carbon Nanotube Microcapsules The lignin-carbon nanotube microcapsules according to example 6 are determined for their size distribution and release amount of core materials, and the results are shown in FIG. 10a and FIG. 10b.

FIG. 10a and FIG. 10b each show the confocal microscopic images of the lignin-carbon nanotube microcapsules obtained according to Example 6. Particularly, FIG. 10a shows a confocal microscopic image of the microcapsules obtained by using a fluorescent material, Coumarin 6, in a core material, i.e., olive oil containing carbon nanotubes therein. Referring to FIG. 10a and FIG. 10b, it can be seen that lignin-carbon nanotube microcapsules including lignin as a shell material and including, as a core material, olive oil containing carbon nanotubes dispersed therein are formed.

What is claimed is:

1. Lignin microcapsules comprising lignin as a shell material and comprising an oil and a carbonaceous material as a core material.

2. The lignin microcapsules according to claim 1, which have a size of 10 nm-1 μm.

3. The lignin microcapsules according to claim 1, which release oil under hydrophobic atmosphere.

4. The lignin microcapsules according to claim 1, wherein the carbonaceous material is carbon nanotubes.

5. The lignin microcapsules according to claim 4, wherein the carbon nanotubes are dispersed carbon nanotubes.

6. The lignin microcapsules according to claim 4, which release carbon nanotubes under hydrophobic atmosphere.

7. The lignin microcapsules according to claim 1, wherein the w/w ratio of lignin/oil is in a range of 5:1 to 20:1.

8. The lignin microcapsules according to claim 1, wherein the lignin is an amount of 5-20 wt %.

9. A lignin microcapsule comprising lignin as a shell and carbon nanotubes in oil as a core.

10. The lignin microcapsule according to claim 9, wherein the shell is configured to release the oil in response to hydrophobic atmosphere or external force.

11. A material comprising a nanofiber or a nanoweb, the material comprising the lignin microcapsule according to claim 9.

* * * * *